(12) United States Patent
Maeda et al.

(10) Patent No.: US 6,605,720 B1
(45) Date of Patent: Aug. 12, 2003

(54) PROCESS FOR MAKING SPIROLACTONE COMPOUNDS

(75) Inventors: Kenji Maeda, Aichi (JP); Shinji Kato, Aichi (JP); Takehiko Iida, Aichi (JP); David M. Tschaen, Holmdel, NJ (US)

(73) Assignees: Merck & Co., Inc., Rahway, NJ (US); Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/349,835

(22) Filed: Jan. 23, 2003

Related U.S. Application Data
(60) Provisional application No. 60/352,451, filed on Jan. 28, 2002.

(51) Int. Cl.[7] ............................................. C07D 491/107
(52) U.S. Cl. ............................................................ 546/15
(58) Field of Search ............................................ 546/15

(56) References Cited

U.S. PATENT DOCUMENTS
6,388,077 B1 * 5/2002 Fukami et al. ................ 546/15

FOREIGN PATENT DOCUMENTS
WO    WO 01/14376 A1    3/2001

OTHER PUBLICATIONS
Epsztajn et al., Monatshefte fur Chemie 121 (1990), pp. 909–921, "Application of organolithium and related reagents in synthesis, Part VI [1] . . . ".

* cited by examiner

*Primary Examiner*—Patricia L. Morris
(74) *Attorney, Agent, or Firm*—Baerbel R. Brown; Catherine D. Fitch; Melvin Winokur

(57) ABSTRACT

This invention relates to processes for making spirolactone compounds analogous to formula I:

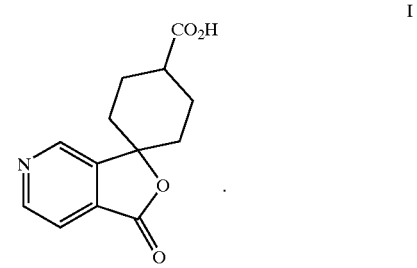

13 Claims, No Drawings

PROCESS FOR MAKING SPIROLACTONE COMPOUNDS

This application claims benefit of priority of provisional application, Ser. No. 60/352,451, filed on Jan. 28, 2002.

BACKGROUND OF THE INVENTION

This invention relates to processes for making spirolactone compounds of formula I. The process involves ortho lithiation of an aromatic compound followed by subsequent addition to a ketone derivative. After acidification, the desired spirolactone derivative is isolated in good yield. A stereoselective reduction of the ketone intermediate generates the desired cis isomer of the alcohol which is subsequently activated and treated with cyanide to form the desired nitrile intermediate. Hydrolysis of the nitrile under acidic conditions selectively generates the trans carboxylic acid product. Crystallization of the carboxylic acid intermediate gives the desired material in highly pure form.

SUMMARY OF THE INVENTION

By this invention, there is provided a process for the preparation of a compound of structural formula I:

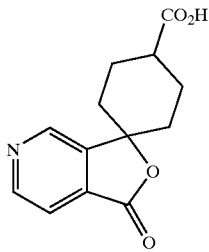

I comprising the steps of:

a. Combining a strong base with phenyl isonicotinamide in an aprotic solvent;

b. Adding a protected ketone;

c. Adjusting the pH with an acid to between 1 and 4 to deprotect the ketone;

d. Treating the ketone with a reducing agent to provide an alcohol;

e. Activating the alcohol to make a leaving group;

f. Displacing the leaving group with cyanide to produce a nitrile;

g. Hydrolyzing the nitrile with aqueous acid to yield the compound of formula I.

DETAILED DESCRIPTION OF THE INVENTION

By this invention, there is provided a process for the preparation of a compound of structural formula I:

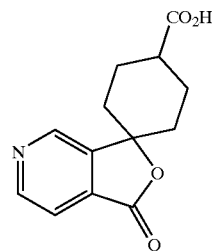

I comprising combining a strong base with phenyl isonicotinamide in an aprotic solvent.

A variety of strong bases can be used in the present invention. In one class of the invention, the strong bases include, but are not limited to n-BuLi, sec-BuLi, t-BuLi, LiHMDS, NaHMDS, KHMDS and LiTMP. In a subclass of the invention, the strong base is n-BuLi.

Various aprotic solvents can be used in the present invention. In one class of the invention, the aprotic solvents include, but are not limited to THF, toluene, heptane, dimethoxyethane, benzene, and hexane, diethyl ether, xylene, and any mixtures thereof. In a subclass of the invention the aprotic solvent is THF.

In one class of the invention, the combination of the strong base and the phenyl isonicotinamide, and the addition of the ketone protecting group are run between −78° C. and 0° C.

The invention is also directed to a process comprising adding a protected ketone after combining a compound of formula I with a strong base and phenyl isonicotinamide in an aprotic solvent.

In one class of the invention, the protected ketone includes, but is not limited to 1,4-cyclohexanedione-monoethylene ketal, dimethyl ketal, diethyl ketal, or 1,3 dithiane, and olefin.

The invention is also directed to a process comprising adjusting the pH with an acid to between 1 and 4 to deprotect the ketone.

In one class of the invention, the pH range includes, but are not limited to 2–3. In a subclass of the invention, the pH is 2.40.

In one class of the invention, the acids used to lower the pH include, but are not limited to hydrochloric, sulfuric, phosphoric, or triflic.

The invention is also directed to a process comprising treating the ketone with a reducing agent to provide an alcohol.

In one class of the invention, the reducing agent includes, but is not limited to sodium borohydride, lithium aluminum hydride, or DIBAL. In another class of the invention, the ketone may be reduced via catalytic hydrogenation.

The invention is also directed to a process comprising activating the alcohol to make a leaving group. By activating the alcohol, the alcohol is converted into a leaving group at that carbon.

In one class of the invention, the leaving group includes, but is not limited to mesylate, tosylate, triflate, and halide.

The invention is also directed to a process comprising displacing the leaving group with cyanide to produce a nitrile.

In one class of the invention the cyanide is selected from the group consisting of sodium cyanide, KCN, $ZnCN_2$, and TMSCN.

The invention is also directed to a process comprising hydrolyzing the nitrile with aqueous acid to produce the compound of formula I. The hydrolyzation liberates the free acid.

In one class of the invention, the aqueous acid includes, but is not limited to sulfuric, hydrochloric, phosphoric, and any mixtures thereof.

In the schemes and examples below, various reagent symbols and abbreviations have the following meanings:

| | |
|---|---|
| n-BuLi: | n-Butyl Lithium |
| $CH_2Cl_2$: | Methylene chloride |
| $CHCl_3$: | Chloroform |
| DMF: | Dimethylformamide |
| DMSO: | Dimethylsulfoxide |
| EtOAc: | Ethyl acetate |
| HCl: | Hydrcholric acid |
| LiTMP | Lithium Tetramethylpiperidide |
| MeCN: | Acetonitrile |
| MTBE: | t-Butyl methyl ether |
| $NaBH_4$: | Sodium Borohydride |
| NaCl: | Sodium chloride |
| NaCN: | Sodium cyanide |
| $NaHCO_3$: | Sodium bicarbonate |
| NaOH: | Sodium hydroxide |
| THF: | Tetrahydrofuran |

EXAMPLE 1

Spirolactone Formation

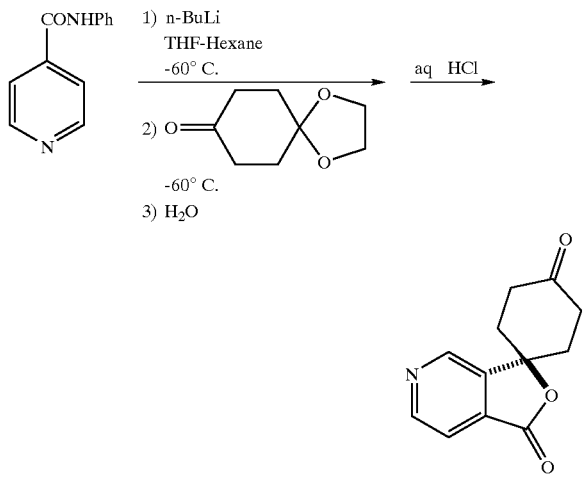

Phenyl isonicotinamide (6.00 g) is charged to a 500mL three-necked flask equipped with $N_2$ line, a thermometer and a stirrer chip. THF (180 mL) is added to the powder and the solution is cooled to −60° C. 1.56 M n-BuLi in hexane (39.8 mL) is added dropwise keeping the temperature below −55° C. After stirring at −60° C. for 2 h, a solution of 1,4-Cyclohexanedione-mono-ethylene ketal (5.67 g) in THF (30 mL) is added dropwise to the resulting orange suspension below −58° C. and the mixture is stirred for 1 h.

The reaction mixture is poured into $H_2O$ (90 mL) and allowed to warm up to room temperature. The aqueous layer is separated and extracted with MTBE two times (60+30 mL). 5N HCl is added to the aqueous layer to adjust the pH to 2.40 while maintaining the temperature below 10° C. The aqueous solution is stirred for 20 h at 65° C. and then cooled to room temperature. After NaCl (23g) is added, the solution is extracted with EtOAc (150 mL) and the organic layer is separated. The aqueous layer is adjusted pH to 4.50 with 4.0 mL of 1N NaOH while keeping the temperature below 10° C. followed by extraction with EtOAc two times (70 mL+40 mL). Combined organic layer was washed with 5% $NaHCO_{3aq}$ (15 mL) and 20% NaCl aq (15 mL).

The organic layer is concentrated to 30 and then 5.3 mL of DMF is added.(The suspension is then warmed to 60° C. After the slurry is dissolved, the solution is cooled to 50° C. and stirred for 30 min. The resulting slurry is then cooled to room temperature. Heptane (76 mL) is added dropwise to the resulting slurry over 1 h and the solution is stirred at 0° C. overnight.

The resulting crystals are filtered and washed with a mixed solvent of EtOAc and heptane (1:5, 24 mL). The resulting wet cake is dried in a vacuum desiccator at 50° C. to yield the spriolactone.

Ketone Reduction

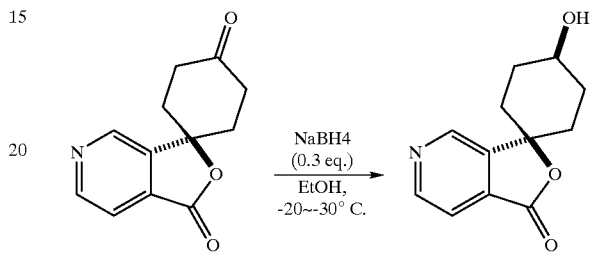

The ketone (5.000 g, 23.02 mmol) is suspended in EtOH (40 mL). $NaBH_4$ (0.261 g, 6.90 mmol, 0.3 eqiv.) is suspended in EtOH (50 mL) in a 200 mL 4-neck round bottomed flask and cooled to −30° C. The above slurry of ketone in EtOH is added to the $NaBH_4$ suspension in EtOH over 20 min below −20° C. and the resulting slurry is stirred at −25~−20° C. for 1 hrs. 25% (w/w) aqueous $NH_4Cl$ (15 mL) is added to the mixture over 5 min below −10° C. Subsequently the mixture is allowed to warm to room temperature and stirred at 20~25° C. for 2 hrs (pH 8.3). EtOAc (150 mL), $H_2O$ (25 mL) and 25% (w/w) aqueous NaCl (5 mL) are added to the slurry. After stirring for 5 min, the organic layer is separated and washed with 25% (w/w) aqueous NaCl (25 mL). After separating, the NaCl aqueous layer is extracted with EtOAc (100 mL). The combined organic solution is concentrated to 25 mL at 40° C. of the bath temperature under the reduced pressure. After adding $H_2O$ (25 mL), the slurry is concentrated to 25 mL volume at 40° C. of the bath temperature under the reduced pressure. Then $H_2O$ (20 mL) and EtOH (5 mL) is added and the batch is aged at 20–25° C. for 3 hrs. The crystals are filtered and washed with $H_2O$ (15 mL). After drying in vacuo overnight at room temperature, the product is obtained as white crystals.

Mesylation

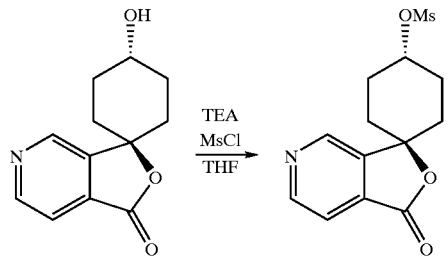

Alcohol (5 g, 22.8 mol) is charged to a 300 mL four-necked flask. THF(100 mL) is added to the powder and the resulting white suspension is cooled to 0–5° C. using ice bath. To the white suspension, TEA (9.6 mL, 68.4 mmol) is added dropwise. After stirring for 30 min, MsCl (2.7 mL, 34.2 mmol) is added dropwise to the solution. The ice bath is removed and the mixture is allowed to warm to room temperature (20 to 25° C.) and stirred for 45 min. Water is added dropwise and EtOAc(50 mL) is added. The water layer is removed, and organic layer is concentrated to 30 mL in vacuo. DMF(16 mL) is added to the residue and the solution is concentrated to 15 mL in vacuo. Water (5 mL) is added dropwise to give slightly turbid solution. Additional water (75 mL) is added dropwise and the resulting mixture is stirred for 10 h. The crystals are filtered off, washed with H$_2$O (50 mL) and dried in vacuo.

Cyanation

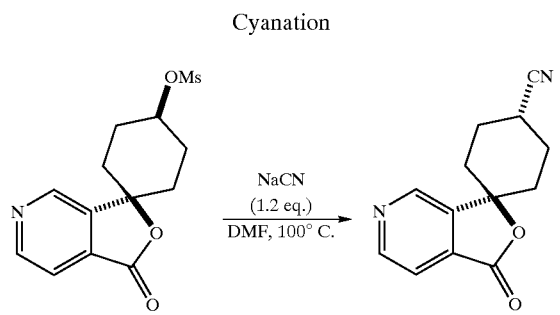

A 2 L four-necked round-bottomed flask, is charged with DMF (650 ml, KF 100 ppm) and the Mesylate (65.0 g) under N$_2$ atmosphere. To the resulting solution, NaCN (12.9 g) is added at room temperature. The suspension is heated to 100° C. and stirred for 16 h.

After being cooled to room temperature, H$_2$O (1300 ml) is added dropwise to the solution with an ice-bath. The resulting suspension is stirred at room temperature for 2 h and filtered. The pale-yellow solid is washed with H$_2$O (130 ml) and dried in vacuo (40° C.) to yield the nitrile.

Hydrolysis

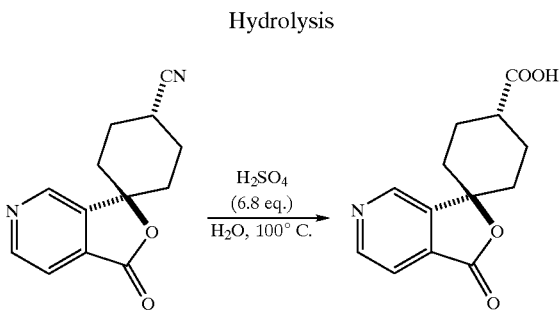

A 1 L four-necked round-bottomed flask is charged with H$_2$O (240 ml) under N$_2$ atmosphere. To the H$_2$O, H$_2$SO$_4$ (99.3 ml) is added. Nitrile is added to the solution. The resulting suspension is warmed to 100° C. and stirred for 16 h.

After being cooled to room temperature, 4N NaOH (ca.830 ml) is added dropwise to the solution until pH is adjusted to 3~3.5. The resulting suspension is stirred at room temperature for 30 min and filtered off. The pale-yellow solid is washed with H$_2$O (120 ml) and dried in vacuo (40° C.) to yield the carboxylic acid.

What is claimed is:

1. A process for preparing a compound of formula I:

comprising the steps of:
   a. Combining a strong base with phenyl isonicotinamide in an aprotic solvent;
   b. Adding a protected ketone;
   c. Adjusting the pH with an acid to between 1 and 4 to deprotect the ketone;
   d. Treating the ketone with a reducing agent to provide an alcohol;
   e. Activating the alcohol to make a leaving group;
   f. Displacing the leaving group with a cyanide to produce a nitrile;
   g. Hydrolyzing the nitrile with aqueous acid to produce the compound of formula I.

2. The process of claim 1 wherein steps a. and b. are run between −78° C. and 0° C.

3. The process of claim 2 wherein the aprotic solvent is selected from the group consisting of THF, toluene, heptane, dimethoxyethane, benzene, and hexane, diethyl ether, xylene, and any mixtures thereof.

4. The process of claim 3 wherein the aprotic solvent is THF.

5. The process of claim 3 wherein the strong base is selected from the group consisting of n-BuLi, sec-BuLi, t-BuLi, LiHMDS, NaHDS, KHMDS and LiTMP.

6. The process of claim 5 wherein the strong base is n-BuLi.

7. The process of claim 5 wherein the protected ketone is selected from the group consisting of 1,4-cyclohexanedione-mono-ethylene ketal, dimethyl ketal, diethyl ketal, 1,3 dithiane and olefin.

8. The process of claim 7 wherein the acid is selected from the group consisting of hydrochloric, sulfuric, phosphoric, or triflic.

9. The process of claim 8 wherein the pH is adjusted to between 2 and 3.

10. The process of claim 9 wherein the reducing agent is selected from the group consisting of sodium borohydride, lithium aluminum hydride, and DIBAL.

11. The process of claim 10 wherein the leaving group is selected from the group consisting of mesylate, tosylate, triflate, and halide.

12. The process of claim 11 wherein the cyanide is selected from the group consisting of sodium cyanide, KCN, ZnCN2, and TMSCN.

13. The process of claim 12 wherein the aqueous acid is selected from the group consisting of sulfuric, hydrochloric, phosphoric, and any mixtures thereof.

* * * * *